United States Patent [19]
Carr et al.

[11] Patent Number: 4,482,472
[45] Date of Patent: Nov. 13, 1984

[54] LIQUID CRYSTAL MATERIALS

[75] Inventors: Neil Carr, Hull; Jennifer Constant, Powick; George W. Gray, Cottingham; Damien G. McDonnell; Edward P. Raynes, both of Malvern, all of England

[73] Assignee: The Secretary of State for Defence in Her Britannic Majesty's Government of the United Kingdom of Great Britian and Northern Ireland, England

[21] Appl. No.: 404,497

[22] Filed: Aug. 2, 1982

[30] Foreign Application Priority Data

Aug. 6, 1981 [GB] United Kingdom ............... 8124044
Aug. 6, 1981 [GB] United Kingdom ............... 8124045
Jun. 15, 1982 [GB] United Kingdom ............... 8217356

[51] Int. Cl.$^3$ .......................... C02F 1/13; C09K 3/34
[52] U.S. Cl. ............................ 252/299.1; 252/299.5; 252/299.6; 252/299.62; 252/299.63; 252/299.61; 350/346; 350/347 E; 350/349; 350/350 R
[58] Field of Search ............... 252/299.62, 299.63, 252/266.6, 299.5, 299.1, 299.61; 350/350 R, 349, 346, 347 E

[56] References Cited

U.S. PATENT DOCUMENTS 3,387,051  6/1968  Norell ........................... 252/299.6
4,035,056  7/1977  Coates et al. ................. 252/299.66
(List continued on next page.)

FOREIGN PATENT DOCUMENTS 56113  7/1982  European Pat. Off. ........ 252/299.63
(List continued on next page.)

OTHER PUBLICATIONS

Praefcke, K., et al., Chemiker-Zeitung, vol. 104, No. 9, pp. 269-271 (1980).
Beilsteins Handbuch der Organische Chemie 4th Edn, Supplement 4, volume 5, 1979 pp. 1453 lines 17-26.

*Primary Examiner*—Teddy S. Gron
*Attorney, Agent, or Firm*—Cushman, Darby & Cushman

[57] ABSTRACT

A liquid crystal material which comprises a mixture of compounds includes at least one low viscosity additive compound of Formula (I) as follows:

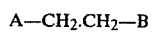

Formula (I)

wherein A is selected from:

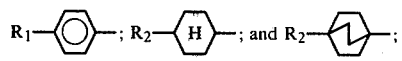

and B is selected from:

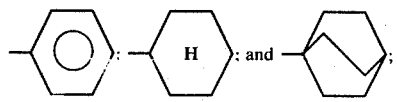

where $R_1$ is selected from alkyl, alkoxy, alkylcarbonyloxy and alkoxycarbonyloxy; and $R_2$ is alkyl; and where

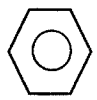

is a benzene ring;

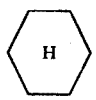

is a cyclohexane ring, which is in the trans-configuration if di-substituted; and

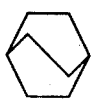

is a bicyclo(2,2,2)octane ring.

23 Claims, 7 Drawing Figures

U.S. PATENT DOCUMENTS

| | | | |
|---|---|---|---|
| 4,118,335 | 10/1978 | Krause et al. | 252/299.5 |
| 4,180,475 | 12/1979 | Schant et al. | 252/299.5 |
| 4,198,130 | 4/1980 | Boller et al. | 252/299.5 |
| 4,261,651 | 4/1981 | Gray et al. | 252/299.63 |
| 4,357,078 | 11/1982 | Carr et al. | 252/299.63 |
| 4,393,258 | 7/1983 | Sato et al. | 252/299.63 |
| 4,400,061 | 8/1983 | Carr et al. | 252/299.63 |
| 4,419,263 | 12/1983 | Praefcke et al. | 252/299.63 |
| 4,431,853 | 2/1984 | Sato et al. | 252/299.63 |
| 4,439,015 | 3/1984 | Rich et al. | 252/299.63 |

FOREIGN PATENT DOCUMENTS

| | | | |
|---|---|---|---|
| 3201721 | 8/1982 | Fed. Rep. of Germany | 252/299.63 |
| 3226051 | 2/1983 | Fed. Rep. of Germany | 252/299.63 |
| 3237367 | 4/1983 | Fed. Rep. of Germany | 252/299.63 |
| 57118526 | 7/1982 | Japan | 252/299.63 |
| 2092146 | 8/1982 | United Kingdom | 252/299.63 |
| 2093057 | 8/1982 | United Kingdom | 252/299.63 |

LIQUID CRYSTAL MATERIALS

The crystal invention relates to liquid crystal materials and additives for use in them.

The use of liquid crystal materials to exhibit electro-optical effects in display devices such as digital calculators, watches, meters and simple word displays is now well known. However known liquid crystal materials are not ideal in all respects and a considerable amount of work is currently being carried out in the art to improve their properties. Liquid crystal materials normally consist of mixtures of compounds and improved materials are obtained by forming new mixtures having an improved combination of properties.

Although liquid crystal materials normally consist mainly of compounds which exhibit a liquid crystal phase by themselves the materials may contain components which do not exhibit such a phase. Compounds forming such components exhibit a virtual or monotropic liquid crystal to isotropic liquid transition (clearing point) at a temperature below their melting point. As is well known to those skilled in the art monotropic or virtual transitions may be detected respectively by rapid cooling of the liquid phase or by dissolving the compound in a material exhibiting a liquid crystal phase, observing the change in the transition to the isotropic liquid phase of the material by the addition and calculating the virtual transition temperature by extrapolation of the data from a series of such mixtures of known composition.

Compounds which do not exhibit a liquid crystal phase by themselves are useful as additives to liquid crystal materials, e.g. to improve the liquid crystal temperature range (i.e. the range over which the material exhibits a liquid crystal phase) and/or to improve the viscosity of the liquid crystal material.

The liquid crystal temperature range of a material is important because it determines the operating temperature range of the display device. This range is desirably as great as possible.

The viscosity of a liquid crystal material is important because it determines the speed of response of the display device, i.e. the times required to switch the display from the off state to the on state and vice versa. The viscosity is desirably as low as possible. The viscosity of a mixture of compounds forming a liquid crystal material is determined by the viscosity of the individual compounds.

Strictly speaking, the response times are dependent on a number of viscosity coefficients but the main coefficient to be considered is that known as the "flow aligned" viscosity coefficient (see for example the article entitled "Flow aligned viscosities of cyanobiphenyls" by J. Constant and E. P. Raynes Mol. Cryst. Liq. Cryst. (1980) Vol 62 pages 115–124). The term "viscosity" as used in this specification is to be understood to mean the flow aligned coefficient in the nematic liquid crystal phase (mesophase) unless otherwise specified.

Ethyl bridged compounds, i.e. compounds containing the bridging group —CH$_2$.CH$_2$—, are known and are described for example in UK Pat. No. 1,551,043 and UK Patent Application GB No. 2023136A and GB No. 2093057A and are proving to be an attractive family of compounds for use in liquid crystal materials. However, although compounds of this family are known with reasonably low melting points and viscosities these properties are not ideal and could be improved.

It is an object of the present invention to provide a class of compounds belonging to the family of ethyl bridged compounds for use as low viscosity, low melting point additives to liquid crystal materials in order to improve (i.e. reduce) the melting point and/or viscosity of such materials.

According to the present invention there is provided a liquid crystal material which comprises a mixture of compounds and includes at least one low viscosity additive compound characterised in that the material includes one or more low viscosity additive compounds of Formula (I) as follows:

A—CH$_2$.CH$_2$—B     Formula (I)

wherein A is selected from:

and B is selected from:

where R$_1$ is selected from alkyl, alkoxy, alkylcarbonyloxy and alkoxycarbonyloxy; and R$_2$ is alkyl; and where is a benzene ring is a cyclohexane ring, which is in the trans-configuration if disubstituted; and is a bicyclo(2,2,2)octane ring.

Thus the ethyl bridged compounds of Formula (I) are compounds having two ring structures A and B, one A containing a terminal substituent group R$_1$ or R$_2$ which is or includes an alkyl group and the other B containing no substituent group.

Formula (I) thus embraces the sub-classes represented by the following formulae:

Formula (Ia)

Formula (Ib)

Formula (Ic)

Formula (Id)

Formula (Ie)

Formula (If)

Formula (Ig)

Formula (Ih)

Formula (Ii)

Of these sub-classes those wherein B= are preferred, particularly those of Formulae (Id) and (Ig), especially those of Formula (Id).

The groups $R_1$ or $R_2$ may be normal or branched chained group containing up to 18 carbon atoms, desirably 1 to 10 carbon atoms. If the group $R_1$ or $R_2$ is branched it may contain a chiral centre.

Preferably $R_1$ is alkyl or alkoxy, desirably n-alkyl containing 1 to 7 carbon atoms.

Of the known ethyl bridged compounds those having a formula

Formula (II)

where $R_A$ is alkyl and $R_B$ is alkyl or alkoxy, show the best combination of low melting point and low viscosity. For example, the compound of Formula (II) wherein $R_A$ is n-$C_5H_{11}$ and $R_B$ is $OC_2H_5$ has a melting point of 18° C. and a viscosity (extrapolated from measurements using a nematic mixture) of 13 cps at 20° C.

The compounds of Formula (I) can, however, show a better combination of melting point and viscosity. For example, the compound of Formula 1a as follows:

Formula 1a has a melting point of −1.5° C. and an extrapolated 'nematic' viscosity of 7.7 cps at 20° C. The extrapolated nematic viscosity is reduced to 2.2 cps at 20° C. for the n-propyl homologue of the compound of Formula 1a. Thus, the compounds of Formula (I) are very attractive as low melting point, low viscosity additives to liquid crystal materials. These compounds do not necessarily show a liquid crystal phase themselves but they can be added in concentrations of up to 50 per cent (by weight of the overall mixture) to liquid crystal materials without affecting the basic liquid crystalline nature of the material. They will however affect the physical properties of the material and can, for example, provide a liquid crystalline mixture having a reduced melting point and/or a reduced viscosity from the material to which they are added.

The compounds of Formula (I) may be prepared by routes in which the individuall procedures involved are known, the overall routes being new. For example, the following routes may be used:

where $A_1$ is a group containing a benzene ring prepared by Route (1) or Route (2) and the corresponding group $A_2$ is a group containing a cyclohexane ring produced by hydrogenation of the benzene ring. The compound $A_1$—$CH_2.CH_2$—$B_1$ is produced by Route (1) or Route (2).

Since the hydrogenation procedure in Route (3) is not stereospecific, this method can only be used to convert compounds of Formula (Ib) into those of Formula (Ic).

where R'₁=methoxy and R'₂=alkanoyloxy or alkoxycarbonyloxy. In this case the starting material is prepared by Route (1) or Route (2).

The compounds of Formula (I) have a small dielectric anisotropy (when added to liquid crystal materials) and may be added to liquid crystal materials of positive or negative dielectric anisotropy, known and referred to herein respectively as "positive" or "negative" materials, without significantly affecting the dielectric anisotropy of such materials. As is well known to those skilled in the art the dielectric anisotropy of the liquid crystal material is necessary to give electro-optical operation and its sign (for a given frequency) is chosen according to the kind of electro-optical device in which the material is to be used.

Normally, the liquid crystal material in which the compound of Formula (I) is contained will comprise a host material which comprises one or more liquid crystal compounds having a low melting point (<80° C.) which preferably together with the additive(s) show a liquid crystal phase at room temperature together with one or more additives, e.g. to reduce viscosity and/or enhance liquid crystal temperature range, the additive(s) including at least one compound of Formula (I).

The upper limit of the percentage by weight which the compound(s) of Formula (I) constitute in the mixture with the host material will depend on the host material but typically the compound(s) will form between 2 and 50% by weight in total, for example between 5 and 30% by weight inclusive in total.

The host material to which the compound(s) of Formula (I) is added may be one of the following materials:

(i) a positive nematic material for use in twisted nematic effect devices including multiplexed devices; an example of such a device is given below;

(ii) a negative material preferably also with a pleochroic dye, for use in Fréedricksz effect devices (negative nematic type) in which the molecular arrangement may be changed from the homotropic texture (OFF state) to the homogeneous texture (ON state) by an electric field; an example of such a device is given below;

(iii) a positive nematic material, preferably also with a pleochroic dye for use in Fréedricksz effect devices (positive nematic type) in which the molecular arrangement may be changed from the homogeneous texture (OFF state) to the homeotropic texture (ON state) by an electric field;

(iv) a negative material which is a cholesteric (chiral nematic) of suitable resistivity (about 10⁹ ohm-cm), for use in cholesteric memory mode devices in which the molecular arrangement may be changed from a homogeneous texture (OFF state) to a turbulent scattering focal conic texture (ON state) by an electric field;

(v) a strongly negative material which is a cholesteric, preferably together also with a pleochroic dye, for use in cholesteric-to-nematic phase change effect devices (positive contrast type) in which the molecular arrangement may be changed from a weakly scattering, i.e. clear, surface aligned homeotropic texture (OFF state) to a strongly scattering twisted homogeneous texture (ON state) by an electric field;

(vi) a positive material which is a cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field;

(vii) a negative nematic material of suitable resistivity (about 10⁹ ohm-cm), in dynamic scattering effect devices in which the molecular arrangement may be changed from a clear homeotropic texture (OFF state) to a turbulent scattering texture (ON state) by an electric field;

(viii) a positive nematic material in two frequency switching effect devices (which may be twisted nematic effect devices) in which the dielectric anisotropy of the material may be changed from (at low frequency) positive (OFF state) to negative (ON state) by the application of a high frequency electric field.

The construction and operation of the above devices and the general kinds of material which are suitable for use in them are themselves known.

The host material to which one or more compounds of Formula (I) are added may itself be a mixture of two or more compounds selected for the particular device application.

Where a host material is for use in a twisted nematic effect, cholesteric to nematic phase change effect (negative contrast type) or Fréedericksz effect (positive nematic type) device the material preferably contains one or more compounds selected from the following families to give a liquid crystal phase at room temperature as well as a positive dielectric anisotropy.

Formula (IIIa)

Formula (IIIb)

Formula (IIIc)

Formula (IIId)

Formula (IIIe)

Formula (IIIf)

where the various groups R are the same or different alkyl groups (preferably n-alkyl having up to 10 carbon atoms).

The material may also contain one or more high clearing point compounds (typically up to about 35% by weight) of the following classes to extend the liquid crystal temperature range of the material at its upper end:

Formula (IVa)

Formula (IVb)

Formula (IVc)

Formula (IVd)

Formual (IVe)

Formula (IVf)

Formula (IVg)

Formula (IVh)

where R is as defined above.

The compounds of Formula (I) are particularly suitable for use in liquid crystal materials which may be used in multiplexed twisted nematic effect devices. As taught in published UK Patent Applications Nos. 2,031,010A and 2,063,287A the multiplexibility of a strongly positive host material, eg consisting of biphenyl compounds of Formula (IIIa) and/or the PCH compounds of Formula (VIIb), together with one or more high clearing point compounds selected from the classes of Formulae (IVa to h), may be improved by the addition of a component of low dielectric anisotropy. This improvement is believed to be brought about by the disruption of anti-parallel pairing of the molecules of the cyano compounds caused by introduction of the material of low dielectric anisotropy.

The component of low dielectric anisotropy may comprise one or more compounds of Formula (I) optionally together with one or more compounds selected from the following known families.

Formula (Va)

Formula (Vb)

Formula (Vc)

Formula (Vd)

Formula (Ve)

Formula (Vf)

Formula (Vg)

Formula (Vh)

Formula (Vi)

-continued

Formula (Vj)

Formula (Vk)

where X=halo, preferably fluoro,

=bicyclo(2,2,2)octane and R is as defined above.

A multiplexed twisted nematic device may also contain a small amount, eg up to about 2% by weight, of a chiral additive, eg the BDH compound C 15.

Thus, a liquid crystal material suitable for a multiplexed twisted nematic effect device embodying the present invention preferably comprises the components in Table 1 as follows:

TABLE 1

Liquid crystal material composition for multiplexed twisted nematic operation

| Component | Constituents | Percentage by weight |
|---|---|---|
| Component 1: low melting point positive compound(s) giving a room temperature nematic phase. | One or more compounds selected from Formulae (IIIa) to (IIIe) above. | 5–80%, preferably 40–70% |
| Component 2: high clearing point liquid crystal compound(s). | One or more compounds selected from Formulae (IVa) to (IVh). | 5–30%, preferably 10–30% |
| Component 3: low dielectric anisotropy compound(s). | One or more compounds of Formula (I) optionally together with one or more compounds selected from Formulae (Va) to (Vk). | 5–90%, preferably 20–50% |
| Component 4: chiral compound(s) | One or more chiral compounds. | 0–2% |

The compound(s) of Formula (I) preferably constitute from 5 to 30% by weight of the overall material composition.

In the material whose composition is defined by Table 1 the compound(s) of Formula (I) not only help to reduce the viscosity and extend the temperature range of the nematic liquid crystal phase of the mixture at the lower end but also help to improve the multiplexibility of the mixture.

Liquid crystal mixtures including compounds of Formula (I) may be formed in a known way, eg simply by heating the constituent compounds to form an overall isotropic liquid, stirring the liquid for a short period, eg about 10 minutes, and allowing it to cool.

To prevent more general examples of a mixture according to the second aspect at least one compound according to Formula (I) above may be mixed together with one or more compounds in any one or more of the following known families for use in one or more of the applications given above (the actual application(s) depending on the mixture's properties):

i ii iii iv v vi vii viii ix x xi xii xiii

-continued

; m = 1,2

-continued xiv xv where xvi is a trans-1,4-disubstituted cyclohexane ring, xvii is a 1,4-disubstituted bicyclo(2,2,2)octane ring, X is a 1,4 phenylene group xviii xix a 4,4' biphenylyl group xx a 2,6 naphthyl group xxi xxii xxiii or a trans-1,4-disubstituted cyclohexane ring, and $Y_1$ is CN, or R' or CO.O—X—$Y^1$ where $Y^1$ is CN, or R' or OR'; where R and R' are alkyl groups; or a derivative of one of these wherein H is replaced by a halogen, eg F, in one of the benzene rings.

xxiv Preferably, the compound(s) of Formula (I) comprises between 5 and 30% by weight of the mixture.

xxv According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula (I) above.

xxvi

The device according to the second aspect may be a twisted nematic effect device, which may or may not be operated in a multiplexed fashion, a cholesteric-to-nematic phase change effect device, a Fréedericksz effect device or a two-frequency switching effect device, all constructed in a known manner or any of the other devices mentioned above. The various ways in which compounds according to Formula (I) may be used in these devices are outlined above and will be further apparent to those skilled in the art.

Examples of the preparation and properties of compounds having Formula (I) will now be given. The symbols used in the Examples have the following meanings:

| | |
|---|---|
| N = | nematic liquid crystal. |
| I = | isotropic liquid. |
| N-I = | nematic to isotropic liquid transition temperature (clearing point). |
| square brackets [ ] around a temperature value indicate a virtual transistion. | |
| mp = | melting point. |
| bp = | boiling point. |
| η = | viscosity. |

EXAMPLE 1

This example describes the preparation of 1-(trans-4'alkyl cyclohexyl)-2-phenylethanes by the following route:

R₂—⟨H⟩—CH₂.CO₂H  STEP A1 →

R₂—⟨H⟩—CH₂.OC—⟨O⟩

↓ STEP B1

R₂—⟨H⟩—CH₂.CH₂—⟨O⟩ where $R_2$ is an alkyl group. This is an example of Route (1) specified above.

STEP A1

The production of trans-4-alkylcyclohexylmethyl phenyl ketones from trans-4-alkylcyclohexylacetic acid.

This step may be carried out essentially by the same method as for Friedel-Crafts acylation of benzene using the appropriate trans-4-alkylcyclohexylacetic acid (which is first converted to the acid chloride) as described in the literature. See for example, AI Vogel, Textbook of Practical Organic Chemistry, 4th Edition, 770 (1978).

An example of such a product is trans-4-n-propylcyclohexylmethyl phenyl ketone, mp 46° C.

STEP B1

The production of 1-(trans-4'-alkylcyclohexyl)-2-phenylethanes from trans-4-alkylcyclohexylmethyl phenyl ketones.

This step may be carried out essentially by one of the methods described in the literature for the reduction of a ketone to a hydrocarbon—see for example the method described by D Coates and GW Gray, J Chem Soc, Perkin II, 7, 867 (1976) which uses a 4-(4"-n-alkoxyphenylacetyl)-4'-bromobiphenyls.

Examples of such products are

Formula 1b bp=113° C. at 0.5 mm Hg
N-I=[−55] (by extrapolation)
η20° C.=8.5 cps (isotropic liquid state)
mp=3° C. and Formula 1a bp=120° C. at 0.1 mm Hg
N-I[−30] (by extrapolation)
mp=−1.5° C.

Formula 1c mp=+1° C.
N-I=[−75° C.] (by extrapolation)

Formula 1d mp=12° C. (measured by differential scanning calorimetry)
N-I=[−66° C.]
Activation energy=6.3 kCal/mole
η at 20° C. (isotropic liquid state)=10.8 cps
η at 0° C. (isotropic liquid state)=24 cps The viscosity of the compound of Formula (VIb) measured as an isotropic liquid is as specified in Table 2 as follows:

TABLE 2

| Viscosity of the compound of Formula 1a measured as an isotropic liquid | |
|---|---|
| Viscosity (cSt) | Temperature (°C.) |
| 30.8 | 0 |
| 13.4 | 20 |
| 9.2 | 30 |
| 7.2 | 40 |
| 5.5 | 50 |
| 4.4 | 60 |

Using a 20% mixture of the compound of Formula 1b in the commercially available material ZLI 1132 supplied by E Merck Co the viscosity of the nematic phase of the solution was measured and found to be 16.8 cps at 20° C. From the expression:

$$\log \eta = C_1 \log \eta_1 + C_2 \log \eta_2 \qquad \text{Equation 1}$$

where η is the viscosity of the mixture, C₁ and η₁ are respectively the concentration and viscosity of one component of the mixture—the compound of Formula (VIa)—and C₁ and η₂ are respectively the concentration and viscosity of the other component of the mixture—ZLI 1132—the value of 2.2 cps was obtained for the viscosity η₁. This means that the viscosity of the compound of Formula 1b has an effective viscosity of 2.2 cps at 20° C. when contained in a material exhibiting a nematic liquid crystal phase at that temperature.

Extrapolated viscosities of 7.7 cps, and 24.5 cps at 20° C. were respectively obtained in a similar way for the 'nematic' phase of the compounds of Formula 1a, 1c and 1d.

Examples of compounds (including those of Formula 1b and 1a) which may be made by the method of Example 1 are as listed in Table 3 as follows:

TABLE 3

Compounds of Formula

| $R_2$ | $R_2$ continued | $R_2$ continued |
|---|---|---|
| CH₃ | n-C₇H₁₅ | 1-methylpropyl |
| C₂H₅ | n-C₈H₁₇ | 2-methylbutyl |
| n-C₃H₇ | n-C₉H₁₉ | 3-methylpentyl |
| n-C₄H₉ | n-C₁₀H₂₁ | 4-methylhexyl |
| n-C₅H₁₁ | n-C₁₁H₂₃ | |
| n-C₆H₁₃ | n-C₁₂H₂₅ | |

EXAMPLE 2

This example describes the preparation of 1-(trans-4'-alkylcyclohexyl)-2-cyclohexylethanes by the following route:

where R₂ is an alkyl group. This is an example of Route (3) specified above.

STEP A2

The production of 1-(trans-4'-alkylcyclohexyl)-2-cyclohexyl-ethanes from 1-(trans-4'-alkylcyclohexyl)-2-phenylethanes (produced in Example 1 above).

This step may be carried out essentially by one of the methods described in the literature for the hydrogenation of an aromatic ring to an alicyclic ring. See for example, RL Augustine, Catalytic Hydrogenation: Techniques and Applications in Organic Synthesis, Arnold, London, p72 (1965).

Examples of compounds which may be made by the method of Example 2 are as specified in Table 4 as follows:

TABLE 4

Compounds of Formula

| $R_2$ | $R_2$ continued | $R_2$ continued |
|---|---|---|
| CH₃ | n-C₇H₁₅ | 1-methylpropyl |
| C₂H₅ | n-C₈H₁₇ | 2-methylbutyl |
| n-C₃H₇ | n-C₉H₁₉ | 3-methylpentyl |
| n-C₄H₉ | n-C₁₀H₂₁ | 4-methylhexyl |
| n-C₅H₁₁ | n-C₁₁H₂₃ | |
| n-C₆H₁₃ | n-C₁₂H₂₅ | |

EXAMPLE 3

This example describes the preparation of 1-(4'-substituted phenyl)-2-cyclohexylethanes by the following route:

This is an Example of Route (2) specified above. In this example the case of R₁=alkyl will be described only although the same method may be used in the cases where R₁=alkoxy.

STEP A3

The production of 4-alkylphenyl cyclohexylmethyl ketones from the commercially available cyclohexylacetic acid.

This step may be carried out essentially by the method used in Step A1 above (which uses the trans-4-alkylcyclohexylacetic acids as starting materials).

STEP B3

The production of 1-(4'-alkylphenyl)-2-cyclohexylethanes from 4-alkylphenyl or cyclohexylmethyl ketones.

This step may be carried out essentially by the method given in Step B1 above (which uses the trans-4-alkylcyclohexylmethyl phenyl ketones as starting materials).

Examples of compounds which may be made by the method of Example 3 are specified in Table 5 below.

EXAMPLE 4

This example describes the preparation of 1-'-substituted phenyl)-2-cyclohexylethanes by the following route:

where $R_X$ is alkyl. This is an example of Route 4 above.

STEP A4

The starting material which is the compound of Formula (IV) wherein $R_1$=methoxy is made previously by the method of Example 3. This compound is demethylated (eg by heating the compound with a mixture of constant boiling hydrobromic acid and acetic acid) according to conventional procedures.

STEP B4

The phenol produced by Step A4 is esterified with the appropriate acid chloride $R_XCO.Cl$ by a known procedure—see for example the method described by G. W. Gray and D. G. McDonnell in Mol. Cryst. Liq. Cryst. Vol 53, page 162 (1979).

STEP C4

The phenol produced by Step A4 is esterified in a manner similar to Step B1 but using the appropriate alkyl chloroformate $ClCO.OR_X$.

Examples of compounds which may be made by the method of Example 4 are as follows:

TABLE 5

Compounds of Formula:

| R' | R' continued | R' continued |
|---|---|---|
| CH₃ | n-C₇H₁₅ | 1-methylpropyl |

TABLE 5-continued

Compounds of Formula:

| R' | R' continued | R' continued |
|---|---|---|
| C₂H₅ | n-C₈H₁₇ | 2-methylbutyl |
| n-C₃H₇ | n-C₉H₁₉ | 3-methylpentyl |
| n-C₄H₉ | n-C₁₀H₂₁ | 4-methylhexyl |
| n-C₅H₁₁ | n-C₁₁H₂₃ | |
| n-C₆H₁₃ | n-C₁₂H₂₅ | |

EXAMPLE 5

The preparation of compounds of Formula (Ig) (as specified above).

The route used is as follows:

where R=n-alkyl; Ts=toluene-4-sulphonyl.

STEP A5: The production of 4-n-alkylbicyclo(2.2.2) octylmethan-1-ols.

Step A may be carried out essentially by the same procedure of Step B2 described in published UK Patent Application No. 2,070,594A.

STEP B5: The production of 4-n-alkylbicyclo(2.2.2) octyl-1-methyl toluene-4-sulphonates.

Step B may be carried out essentially by the procedure of Step B described in published UK Patent Application No. 2,070,594A.

STEP C5: The production of 4-n-alkylbicyclo(2.2.2) octy-1-acetonitriles.

Step C may be carried out essentially by one of the known methods described in the literature for the conversion of a toluene-4-sulphonic acid ester into the corresponding nitrile. See for example Journal of Medicinal Chemistry 10 517 (1967) and Journal of the American Chemical Society 84 3412 (1962).

STEP D5: The production of 4-n-alkylbicyclo(2.2.2) octyl-1-1-acetic acids.

Step D may be carried out essentially by one of the known methods described in the literature for the hydrolysis of a nitrile to a carboxylic acid under acid conditions. For example the following method may be used:

The cyanide (0.117 mole) is heated under gentle reflux for 18 hrs in a mixture of 50% (by wt) aqueous sulphuric acid (100 g) and glacial acetic acid (200 cm$^3$). The cooled solution is shaken with dichloromethane ($4\times100$ cm$^3$) and the combined organic extracts are washed with water ($3\times80$ cm$^3$). The solution is dried (Na$_2$So$_4$), filtered and the solvent removed in vacuo. The product is crystallised (twice) from light petroleum (bp 40-60° C.).

STEP E5: The production of 4-n-alkylbicyclo(2.2.2) octyl-1-methyl phenyl ketones.

Step E may be carried out in essentially the same way as Step A1 described in UK Patent Application No. 8124045 (used for the production of the corresponding cyclohexyl compounds).

STEP F5: The production of 1-(4'-n-alkylbicyclo(2'.2'.2') octyl-2-phenylethanes.

Step F5 may be carried out essentially in the same way was Step B1 described in UK Patent Application No. 8124045 which is used for the preparation of the corresponding cyclohexyl compounds.

Examples of compounds which may be made by this method are listed in Table 6 as follows:

TABLE 6

Compounds of Formula

R—◇—CH$_2$.CH$_2$—◯

| R | R continued |
|---|---|
| CH$_3$ | n-C$_8$H$_{17}$ |
| C$_2$H$_5$ | n-C$_9$H$_{19}$ |
| n-C$_3$H$_7$ | n-C$_{10}$H$_{21}$ |
| n-C$_4$H$_9$ | n-C$_{11}$H$_{23}$ |
| n-C$_5$H$_{11}$ | n-C$_{12}$H$_{25}$ |
| n-C$_6$H$_{13}$ | CH$_3$.CH$_2$.CH(CH$_3$)CH$_2$ |
| n-C$_7$H$_{15}$ | |

The compound of formula has been found to have the following properties: mp=24°; N-I=(+8.5° C.); η(isotropic liquid state at 20° C.) =38 cps; η(nematic phase: obtained from a 20% solution in ZLI 1132 at 20° C.)=24.5 cps.

Examples of materials and devices embodying the invention will now be described by way of example only with reference to the accompanying drawings wherein.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
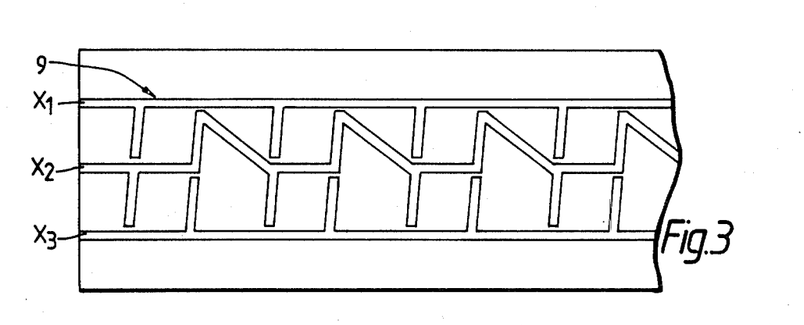
FIG. 3 shows a raar electrode configuration for FIG. 1.
Figure 4:
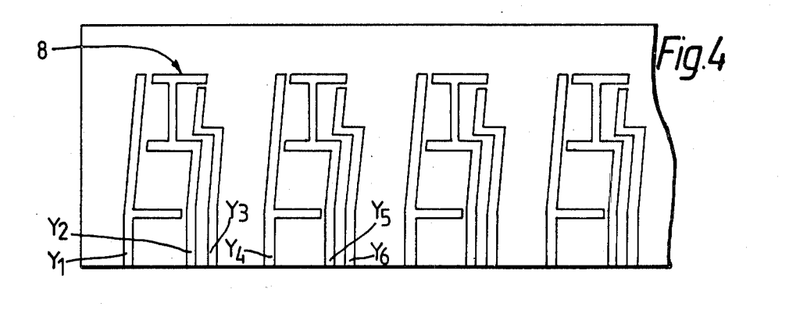
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similary the front electrode structure is formed into three electrodes per digit and decimal point $y_1$, $y_2$, $y_3$..... Examination of the six electrodes per digit shows tha each of the eight elements can independently have a voltage applied thereto by application of suitable voltage to appropriate x, y electrodes.

Figure 1:
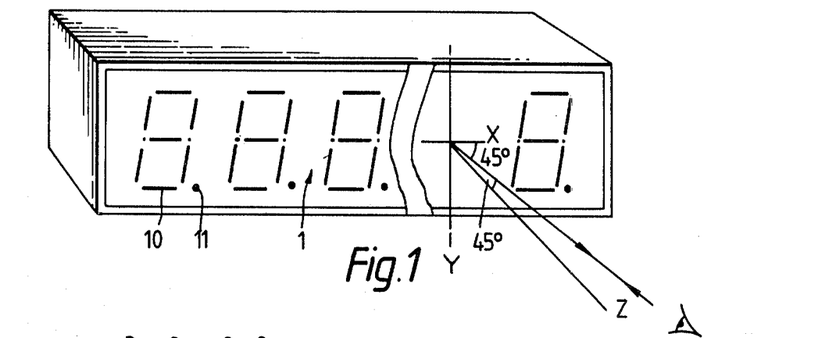
FIG. 1 is a sectional view of a twisted nematic digital display.
Figure 2:
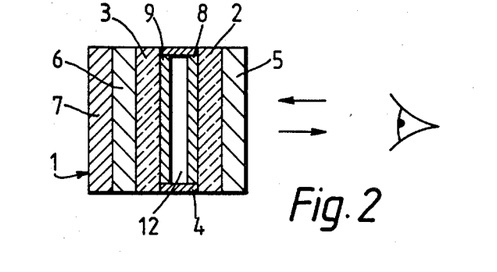
FIG. 2 is a sectional view of the display shown in FIG. 1.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2,3, i.e. along the axis Z. Thus light at the position does not reach the reflector 7 and does not reflect back to the observer who sees a dark display of one or more bars of a digit 10.

Figure 5:
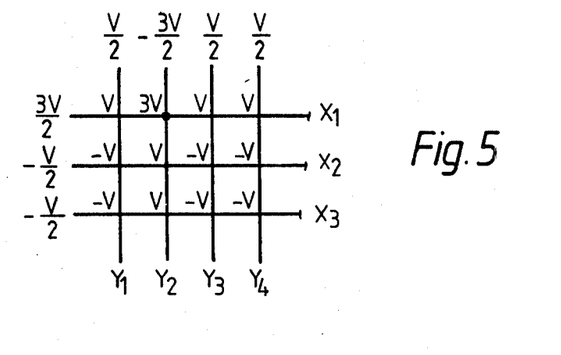
FIGS. 5, 6, 7 show schematic views of the device of FIGS. 1 to 4 with typical addressing voltages.
Figure 6:
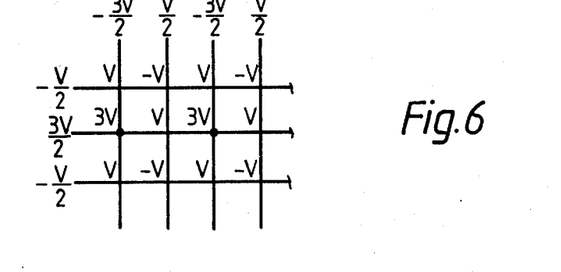
Figure 7:
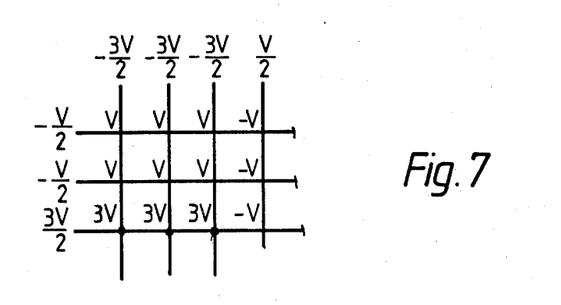

Voltages are applied as follows as shown in FIGS. 5, 6 and 7 for three successive time intervals in a linescan fashion. An electrical potential of $3V/2$ is applied to, i.e. scanned down, each x electrode in turn whilst $-V/2$ is applied to the remaining x electrodes. Meanwhile $-3V/2$ or $V/2$ is applied to the y electrodes. A coincidence of $3V/2$ and $-3V/2$ at an intersetion results in a voltage 3 V across the liquid crystal layer 12. Elsewhere the voltage is V or $-V$. Thus by applying $-3V/2$ to appropriate y electrodes as 3V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 1 to 7 is a multiplexed display because the electrodes are shared between ON and OFF intersections or display elements.

A material embodying the second aspect of the invention which is suitable for use in the material 12 in the above device is in Table 7 as follows (Mixture 1).

TABLE 7
Mixture 1

| Compound | Weight Percentage |
|---|---|
| $C_2H_5$—⌬—⌬—CN | 15 |
| $n\text{-}C_4H_9$—⌬—⌬—CN | 23 |
| $C_2H_5$—⌬—COO—⌬—⌬—CN | 12 |
| $n\text{-}C_5H_{11}$—⌬—⌬—⌬—CN | 10 |
| $n\text{-}C_3H_7$—⌬—$CH_2.CH_2$—⌬ | 15 |
| $n\text{-}C_5H_{11}$—⌬—$CH_2.CH_2$—⌬—$OC_2H_5$ | 15 |
| $n\text{-}C_3H_7$—⌬—$CH_2.CH_2$—⌬—$OC_2H_5$ | 10 |

An alternative material for use as the nematic material 12 is Mixture 2 in Table 8 as follows:

TABLE 8
Mixture 2

| Material | Weight percentage |
|---|---|
| ZLI 1289 | 70 |
| $n\text{-}C_3H_7$—⌬—$CH_2.CH_2$—⌬ | 30 |

ZLI 1289 is a commercially available material supplied by E Merck Co which contains cyanobiphenyl and cyanophenylcyclohexane compounds.

Mixture 2 has the following properties (for a 7 μm thick cell).

| | |
|---|---|
| 1. Clearing point | = 26° C. (max) |
| 2. $V_{90}$ (45° C.) at 20° C. | = 0.925 volts |
| 3. $M_{20}$ | = 1.79 |
| 4. $M'_{20}$ | = 1.37 |

Properties 2, 3 and 4 which relate to the multiplexibility of the mixture, are defined in published UK Patent Application GB No. 2061311A. These properties were obtained by measurement at 0° C. and extrapolation.

Small amounts of a cholesteric material may be added to the nematic material to induce a preferred twist in the molecules in the liquid crystal layer. This and the use of appropriate slide surface treatment removes the problems of display patchiness as taught in UK Patent Serial Nos. 1,472,247 and 1,478,592.

Suitable cholesteric materials are:
C15: about 0.1–0.5% by weight and CB15: about 0.01% to 0.05by weight.

Small amounts of pleochroic dye may be added to enhance the display contrast, e.g. one of the anthroquinone dyes described in UK Patent Specification No. 2011940A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic texture) by the lecthin coating. Applications of an appropriate electric field across the material in the ON state re-arranges the molecules parallel to the slide surfaces (homogeneous texture). A pleochoric dye may be incorporated in the liquid crystal material to enhance the contrast between the ON and OFF states.

A Freedericksz effet cell made in the above way may incorporate Mixture 3 below, the cell specing being 10 μm.

TABLE 9
Mixture 3

| Compound | Weight Percentage |
|---|---|
| $n\text{-}C_5H_{11}$—⌬—CO.O—⌬(F)—$C_3H_7\text{-}n$ | 30 |
| $n\text{-}C_4H_9$—⌬—CO.O—⌬(F)—$C_5H_{11}\text{-}n$ | 30 |
| $n\text{-}C_5H_{11}$—⌬—⌬—$C_2H_5$ | 20 |
| $n\text{-}C_3H_7$—⌬—$CH_2.CH_2$—⌬ | 20 |
| Compound A = | |

TABLE 9-continued

Mixture 3

| Compound | Weight Percentage |
|---|---| may optionally be added to Mixture 3 (up to 3% by weight of Mixture 3) as a negative additive.

The preparation of Compound A is described in published UK Patent Application No. 2061256A. About 1% by weight of a known pleochroic dye e.g. 1,5-bis-4"-n-butylphenylaminoanthraquinone may be added to mixture 3 to give a dyed mixture. (Mixture 3A).

When a voltage is applied across the cell, the colour changes from a weakly absorbing state to a strongly absorbing state.

In an alternative embodiment of the invention a (chloesteric-to-nematic) phase change effect device incorporates a material as defined above.

A cell is prepared containing a long helical pitch chloesteric material sandwiched between electrode-bearing glass slides as in the twisted nematic cell described above. However the polarisers and surface preparations for homogeneous alignment, e.g. treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering that the OFF state. This is a 'negative contrast' type of phase change effect device.

If the inner glass slide surfaces are treated, e.g. with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (e.g. % by weight of 1,5-bis-4'n-butylphenylaminoanthraquinone in the case where $\Delta\epsilon$ is positive) to the liquid crystal material.

A suitable positive dielectric anisotropy material, Mixture 4, embodying the invention for use in a phase change effect (negative contrast type) device is:

TABLE 10

Mixture 4

| Compound | Weight Percentage |
|---|---|
| Mixture B { C6H13—⌬—⌬—CN 37.5%<br>n-C4H9—⌬—⌬—CN 37.5%<br>n-C3H7O—⌬—⌬—CN 25% } | 70 |
| n-C5H11—H—⌬—⌬—CN | 10 |
| CB15 = Rc—⌬—⌬—CN | 4 |
| n-C3H7—H—CH2.CH2—⌬ | 16 |

(Rc = 2-methylbutyl)

A suitable negative dielectric anisotropy material embodying the invention for use in a phase change effect (positive contrast type) device, Mixture 5, is as follows:

TABLE 11

Mixture 5

| Material | Weight Percentage |
|---|---|
| Mixture 3 | 99 |
| Rc—⌬—⌬—COO—⌬—Rc | 1 |

(Rc = (+)-2-methylbutyl)

Examples of high birefringence, low viscosity materials of positive dielectric anisotropy suitable for simple twisted nematic displays and which include a compound of Formula (I) are Mixtures 6 and 7 defined in Tables 12 and 13 as follows:

TABLE 12

Mixture 6

| Compound | Weight Percentage |
|---|---|
| n-C5H11—⌬—⌬—CN | 29 |
| n-C7H15—⌬—⌬—CN | 17 |
| n-C3H7—H—⌬—CN | 11 |
| n-C3H7—H—CH2.CH2—⌬ | 15 |
| n-C5H11—⌬—⌬—⌬—CN | 8 |

TABLE 12-continued
Mixture 6

| Compound | Weight Percentage |
|---|---|
| n-C$_5$H$_{11}$—⌬—◯—◯—CN | 10 |
| n-C$_3$H$_7$—⌬—CO.O—◯—⌬—C$_5$H$_{11}$—n | 10 |

TABLE 13
Mixture 7

| Compound | Weight percentage |
|---|---|
| n-C$_5$H$_{11}$—◯—◯—CN | 29 |
| n-C$_7$H$_{15}$—◯—◯—CN | 17 |
| n-C$_3$H$_7$—⌬—CH$_2$.CH$_2$—◯—CN | 11 |
| n-C$_3$H$_7$—⌬—CH$_2$.CH$_2$—◯ | 15 |
| n-C$_5$H$_{11}$—◯—◯—◯—CN | 8 |
| n-C$_5$H$_{11}$—⌬—◯—◯—CN | 10 |
| n-C$_3$H$_7$—⌬—CO.O—◯—⌬—C$_5$H$_{11}$—n | 10 |

Clearing point $(N - I) = 61°$ C.
birefringence $(\Delta n) = 0.17$
viscosity at 0° C.
$(\eta_{0°C.}) = 109$ cps
viscosity at 20° C.
$(\eta_{20°C.}) = 26.5$ cps
$V_{90}(45°)$ at 20° C. $= 1.24$ volts
$M_{20}^1 = 1.82$
$M_{20}^2 = 1.35$ $$\frac{1}{V} \times \left(\frac{dV}{dT}\right)_{0-30°C.} = 0.69\% \text{ per C.°}$$

The last mentioned property is a measure of the temperature dependence of operation over the range 0 to 30° C. V represents threshold voltage and T temperature.

Mixture 4 above is an example of a material embodying the invention which material is suitable for a positive nematic (negative constant) type phase change effect device. In general terms, it will be apparent to those versed in the art that, to form such a material, the liquide crystal material according to the first aspect of the present invention (i.e. containing a compound of Formula (I)) should include a positive host, preferably one or more compounds of Formulae (IIIa) to (IIIf) together with typically up to 10% of a chiral material (one or more chiral compounds) and typically up to 5% by weight of a pleochroic dye (containing one or more dye compounds).

The compound may be used in the compositions of Mixtures 6 and 7 in place of

We claim:
1. A liquid crystal material which comprises a mixture of compounds at least one of which is a low viscosity additive compound wherein the improvement comprises in said low viscosity additive compound being a compound of Formula (I) as follows:

A—CH$_2$.CH$_2$—B     Formula (I)

wherein A is selected from:

and B is selected from:

where
R$_1$ is selected from alkyl, alkoxy, alkylcarbonyloxy, and alkoxycarbonyloxy; and
R$_2$ is alkyl;
and where is a benzene ring;

is a cyclohexane ring, which is in the trans-configuration if di-substituted; and is a bicyclo(2,2,2)octane ring.

2. A material as claimed in claim 1 and wherein the compound of Formula (I) has a formula:

where $R_2$ is an alkyl group.

3. A material as claimed in claim 1 and wherein the compound of Formula (I) has a formula:

where $R_2$ is an alkyl group.

4. A material as claimed in claim 2 and wherein the group $R_2$ is an n-alkyl group having from one to ten carbon atoms inclusive.

5. A material as claimed in claim 1 and wherein the at least one compound of Formula (I) forms between 2% and 50% by weight of the liquid crystal material.

6. A material as claimed in claim 5 and wherein the at least one compound of Formula (I) forms between 5% and 30% by weight of the liquid crystal material.

7. A material as claimed in claim 1 and wherein the at least one compound of Formula (I) is added to a host material to form the liquid crystal material, the host material comprising at least one low melting point compound showing, together with the at least one additive compound of Formula (I), a liquid crystal phase at 20° C.

8. A material as claimed in claim 7 and wherein the material is for use in a liquid crystal electro-optical device selected from the group consisting of:
twisted nematic effect devices, cholesteric to nematic phase change effect devices, and positive nematic type Fréedericksz effect devices; and contains at least one compound selected from the families represented by the following formulae:

Formula (IIIa)

Formula (IIIb)

Formula (IIIc)

Formula (IIId)

Formula (IIIe)

Formula (IIIf)

where the various groups R are the same or different n-alkyl groups having from one to ten carbon atoms.

9. A material as claimed in claim 8 and wherein the material contains at least one high clearing point compound selected from the families represented by the following formulae:

Formula (IVa)

Formula (IVb)

Formula (IVc)

Formula (IVd)

Formula (IVe)

Formula (IVf)

Formula (IVg)

Formula (IVh)

10. A liquid crystal material as claimed in claim 9, and which is suitable for use in a multiplexed twisted nematic effect device and which comprises a mixture of the following components:

Component 1: a % by weight of one or more low melting point positive compounds selected from the families represented by Formulae (IIIa) to (IIIf);
Component 2: b % by weight of one or more high clearing point compounds selected from the families represented by Formulae (IVa) to (IVh);
Component 3: c % by weight of one or more compounds of Formula (I) optionally together with one or more compounds selected from the families represented by the following formulae:

Formula (Va)

Formula (Vb)

Formula (Vc)

Formula (Vd)

Formula (Ve)

Formula (Vf)

Formula (Vg)

Formula (Vh)

Formula (Vi)

Formula (Vj)

Formula (Vk)

where R is n-alkyl having from one to ten carbon atoms and X is F

Component 4: d % by weight of an optically active additive;
a being in the inclusive range 5 to 80
b being in the inclusive range 5 to 30
c being in the inclusive range 5 to 90 and
d being in the inclusive range 0 to 2; the sum a+b+c+d being 100.

11. A material as claimed in claim 10 and wherein
a is in the inclusive range 40 to 70
b is in the inclusive range 10 to 30 and
c is in the inclusive range 20 to 50.

12. A material as claimed in claim 7 and wherein the material is suitable for a cholesteric to nematic phase change effect device and contains up to 10% by weight of a chiral additive material together with up to 5% by weight of a pleochroic dye.

13. An electro-optical liquid crystal device including two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein,
and wherein the improvement comprises the liquid crystal material being the material claimed in claim 1.

14. A material as claimed in claim 1 and wherein the compound of Formula (I) has the formula:

wherein $R_2'$ is an n-alkyl group having between 1 and 7 carbon atoms inclusive.

15. A material as claimed in claim 14 and wherein the said compound has the formula:

16. A material as claimed in claim 14 and wherein the said compound has the formula:

17. A material as claimed in claim 14 and wherein the compound has the formula:

18. A material as claimed in claim 14 and wherein the compound has the formula:

19. A liquid crystal material as claimed in claim 1 and wherein the said compound having Formula (I) has the formula:

wherein $R_2''$ is an n-alkyl group having between 1 and 7 carbon atoms inclusive.

20. A material as claimed in claim 19 and wherein the said compound has the formula:

21. A material as claimed in claim 19 and wherein the compound has the formula:

22. A material as claimed in claim 19 and wherein the compound has the formula:

23. A material as claimed in claim 19 and wherein the compound has the formula:

* * * * *